(12) United States Patent
Birkenbach et al.

(10) Patent No.: US 9,918,797 B2
(45) Date of Patent: Mar. 20, 2018

(54) PATIENT POSITIONING SYSTEM WITH AN ELECTROMAGNETIC FIELD GENERATOR OF AN ELECTROMAGNETIC TRACKING SYSTEM

(75) Inventors: Rainer Birkenbach, Erding (DE); Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 493 days.

(21) Appl. No.: 14/235,190

(22) PCT Filed: Jul. 28, 2011

(86) PCT No.: PCT/EP2011/062999
§ 371 (c)(1),
(2), (4) Date: Jan. 27, 2014

(87) PCT Pub. No.: WO2013/013718
PCT Pub. Date: Jan. 31, 2013

(65) Prior Publication Data
US 2014/0194734 A1   Jul. 10, 2014

(51) Int. Cl.
*A61G 13/12* (2006.01)
*A61B 19/00* (2006.01)
(Continued)

(52) U.S. Cl.
CPC .......... *A61B 19/5244* (2013.01); *A61B 34/20* (2016.02); *A61B 90/14* (2016.02);
(Continued)

(58) Field of Classification Search
CPC ............ A61B 34/20; A61B 2034/2055; A61B 2034/2072; A61B 2090/3983;
(Continued)

(56) References Cited

U.S. PATENT DOCUMENTS 6,198,961 B1 * 3/2001 Stern ................ G01R 33/34084
324/318
6,428,547 B1 * 8/2002 Vilsmeier ................ A61B 5/06
600/424
(Continued)

FOREIGN PATENT DOCUMENTS

DE   10 2008 062 351   6/2010
WO   2010076676         7/2010

OTHER PUBLICATIONS

International Search Report for International Application No. PCT/EP2011/062999 filed Jul. 28, 2011 dated Jul. 4, 2012.
EPO, Intention to Grant, EP2736440, May 11, 2016.

*Primary Examiner* — Ophelia A Hawthorne
(74) *Attorney, Agent, or Firm* — Tucker Ellis LLP

(57) ABSTRACT

A patient positioning system associated with an electromagnetic field generator includes a patient fixation unit for fixing a patient or a part of the patient's body so as to be immobile with respect to the patient positioning system. The patient fixation unit and the electromagnetic field generator are installed so as to retain their position with respect to each other. A method for navigating a patient or a part of the patient's body by means of a medical navigation system is provided, wherein the patient or part of the patient's body is positioned by such a patient positioning system.

18 Claims, 1 Drawing Sheet

(51) Int. Cl.
*A61B 90/14* (2016.01)
*A61B 90/00* (2016.01)
*A61B 34/20* (2016.01)

(52) U.S. Cl.
CPC ............. *A61B 2034/2051* (2016.02); *A61B 2034/2072* (2016.02); *A61B 2090/397* (2016.02); *A61B 2090/3975* (2016.02); *A61B 2090/3983* (2016.02)

(58) Field of Classification Search
CPC ..... A61B 2090/3975; A61B 5/05; A61B 5/06; A61B 6/04; A61B 2034/2051; A61B 2090/397; A61B 90/14; A61G 13/12
See application file for complete search history.

(56) References Cited

U.S. PATENT DOCUMENTS

| | | | |
|---|---|---|---|
| 6,676,669 B2 * | 1/2004 | Charles | 606/1 |
| 2003/0200052 A1 | 10/2003 | Seiler et al. | |
| 2004/0116803 A1 | 6/2004 | Jascob et al. | |
| 2004/0199072 A1 | 10/2004 | Sprouse et al. | |
| 2009/0048509 A1 | 2/2009 | Wu | |
| 2010/0008475 A1 | 1/2010 | Maschke | |
| 2010/0041985 A1 * | 2/2010 | Simon | A61B 6/463 |
| | | | 600/426 |
| 2010/0168556 A1 | 7/2010 | Shen et al. | |
| 2011/0071389 A1 * | 3/2011 | Simon | A61B 6/12 |
| | | | 600/426 |

* cited by examiner

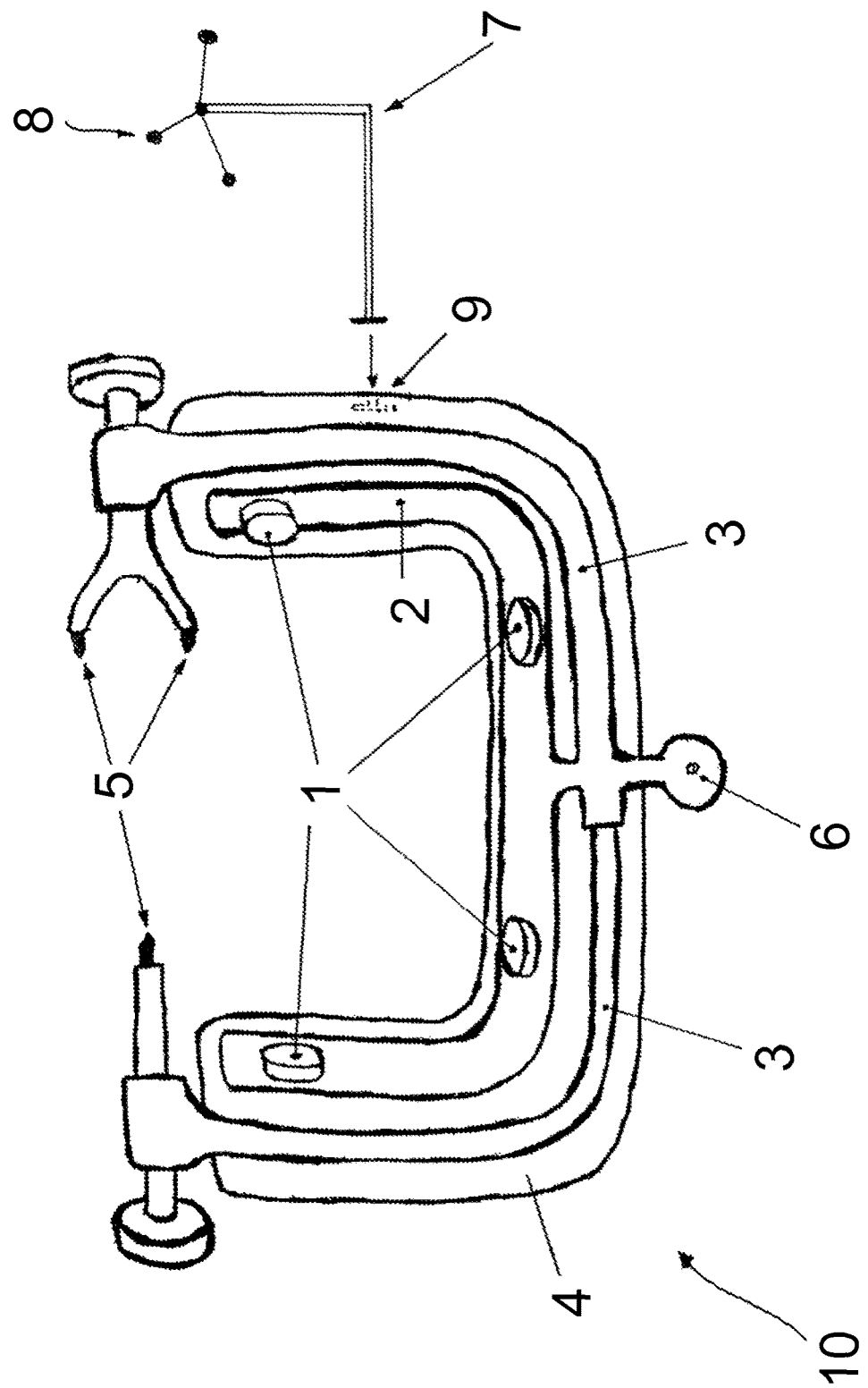

PATIENT POSITIONING SYSTEM WITH AN ELECTROMAGNETIC FIELD GENERATOR OF AN ELECTROMAGNETIC TRACKING SYSTEM

RELATED APPLICATION DATA

This application is a national phase application of International Application No. PCT/EP2011/062999 filed Jul. 28, 2011 and published in the English language.

The present invention relates to a patient positioning system which is associated with an electromagnetic field generator of an electromagnetic tracking system. Electromagnetic tracking systems such as can be used with the present invention are an essential part of medical navigation systems and are used to localise a patient or a part of a patient's body within a certain spatial region, wherein the position of medical devices is determined within said space and in the correct spatial relationship to the patient.

Electromagnetic tracking technology typically suffers from distortions created by devices being used in the vicinity of the generated field or the field generator being used. Metallic objects, ferromagnetic objects and objects made of conductive materials can in particular be sources of such interference and/or distortion. Even some types of carbon-fibre composite can be sources of distortion.

The interference and/or distortion mentioned above are particularly problematic for neurosurgical procedures which on the one hand require highly precise navigation, but on the other hand frequently use potentially disruptive equipment. Even standard head clamps are typically a source of severe distortion which limits the accuracy and reliability of the tracking system.

In addition, the space available for the treatment personnel in the vicinity of the patient is usually quite limited. Positioning an additional electromagnetic field generator in the operating environment creates an even greater strain on the limited available space and may disturb the surgery workflow and constrain the surgeon. Patient positioning devices such as contoured patient support elements on a couch on which elements of an electromagnetic field generator are provided are disclosed for example in US 2004/0199072 A1.

It is an object of the present invention to provide a patient positioning system associated with an electromagnetic field generator, wherein the tracking system's accuracy is optimised in the region of interest (the operating environment). The intention is in particular to minimise interference and/or distortion.

This object is achieved by a patient positioning system associated with an electromagnetic field generator of an electromagnetic tracking system in accordance with claim 1. The sub-claims define advantageous embodiments of the invention.

In accordance with the present invention, the patient positioning system comprises a patient fixation unit for fixing a patient or a part of the patient's body so as to be immobile with respect to the patient positioning system. The fixation unit and the field generator are also installed so as to retain their position with respect to each other.

In other words, the fixation unit and the field generator are positionally integrated into the patient positioning system according to the present invention, i.e. a system which exhibits known and constant positional relationships between its key elements is provided.

Unlike the systems of the prior art such as the one described in the above-mentioned US patent application, the properties of the electromagnetic field in the region of interest, i.e. the operating environment, are well determined and will not be influenced by smaller or larger movements of the system elements or the patient. A constant positional "chain" is retained, starting from the patient or part of the patient's body and including all the elements of the patient fixation system and the elements of the field generator. Thus, the system can be pre-calibrated as a whole, i.e. the distortions in the generated field caused by the patient fixation system can be determined before it is initially used, and interferences and distortions can be compensated for beforehand. A surgeon using the patient positioning system and electromagnetic field generator of the present invention can then immobilise the patient and begin the surgical procedure, wherein none or only minimal distortion compensation work is required at the beginning of the surgical operation.

There are a number of ways of establishing the constant positional relationship of the present invention. One of them is bodily integration, which can in turn be established in various ways, one of which is to integrate the fixation unit and the field generator in general. In another embodiment, the field generator or its elements are integrally mounted, one on top of the other, or are provided as a single integrated unit. It is also possible to mount the fixation unit and the field generator or its elements integrally on a carrier element, in particular on the body of the patient positioning system, wherein the body of the system preferably includes the housing or shell of the patient positioning system.

The advantages of such an integrated system include the fact that the field generator does not have to be set up separately in the vicinity of the region of interest. Thus, the problems of such a field generator occupying space and obstructing the surgeon are eliminated, together with the separate working step of setting up, i.e. positioning, the field generator elements.

In one embodiment of the positioning system of the present invention, a shield is provided for shielding the field generator or its elements from external electromagnetic interference or distortion. Given the above-discussed positionally determined or positionally integrated configuration, and in particular the integrated design, the structure of the patient positioning system of the present invention makes it very easy to determine parts such as the "interior" or "exterior" of the system structure. The interior can mainly include the region of interest or the working region for the surgeon, while the exterior is the portion of the patient's vicinity in which surgical personnel handle instruments which can be a source of interference and/or distortion. Because the exterior can be well-defined, the shield can be placed between said interior and exterior, i.e. can for example be placed optimally in order to prevent external distortion or interference coming from the exterior. One way of achieving this is to locate the shield on the outside of the field generator or its elements, as viewed from the centre portion of the electromagnetic field generated.

Physically, the shield can be mounted on the body of the positioning system, either between the body and the field generator or its elements, or within the body, or on the periphery of the body.

In another advantageous embodiment of the present invention, a tracking reference of a tracking system which employs a modality other than electromagnetism, in particular an optical tracking reference, is assigned to or positioned on the patient positioning system. The advantages of such a configuration will be discussed below.

The system of the present invention can be embodied as a head clamp, in particular a head clamp for neurosurgical procedures, i.e. for fixing a patient's head before neurosurgical steps are performed.

In a second aspect, the present invention relates to a method for navigating a patient or a part of the patient's body by means of a medical navigation system using an electromagnetic tracking system, wherein the patient or part of the patient's body is positioned by a patient positioning system such as has been described above in several embodiments. In the method of the present invention, the distortion and/or interference created by the elements of a certain configuration of the positioning system are determined in a calibration procedure, and the known interference and/or distortion is compensated for in order to use the patient positioning system in said configuration.

As has been mentioned above, the advantages of such a method are that the device is very easy to manage and the positioning system is ready-to-use, all of which results in a high level of tracking accuracy.

It is possible to determine the distortion and/or interference prior to using the patient positioning system in said configuration. However, it is also conceivable to perform a short calibration/compensation step directly after the system has been set up. This calibration/compensation step is easy and simple to perform, since much of the known configuration of the system remains unchanged during set-up.

In one embodiment of the method, a tracking reference of a tracking system which employs a modality other than electromagnetism, in particular an optical tracking reference, is assigned to or positioned on the patient positioning system, and the distortion and/or interference is determined and/or the patient or part of the patient's body is additionally tracked with the aid of said tracking reference.

The invention will now be described in more detail by referring to an embodiment and to the one attached drawing. It should be noted that any of the features of the present invention as referred to here can be implemented separately or in any expedient combination.

The one FIGURE attached schematically shows the design of a neurosurgical head clamp which can act as a patient positioning system in accordance with the present invention.

In the FIGURE, the patient positioning system as a whole has been given the reference numeral 10. It comprises a body or housing 4 which accommodates a head holder bracket 3, wherein the lower centre portion of the head holder bracket 3 comprises a mounting element 6 via which the positioning system 10 as a whole can be mounted, for example to a patient couch. Both ends of the bracket 3 comprise axially adjustable holders for head fixation elements, of which only the head pins have been indicated, by the reference numeral 5.

A shield element 2 is in a constant positional relationship with respect to the bracket 3—in the present embodiment, fixed to the bracket 3—and can be a flat, longitudinally extending body composed of a material which can be used to shield a portion of the adjacent space from any electromagnetic influences induced. Like the bracket 3, the shield 2 exhibits a U-shape which extends in the body 4 in such a way that the system 10 as a whole surrounds a region of interest in which a patient's head can be positioned and immobilised by means of the head pins 5.

An electromagnetic field is created in and around the region mentioned above, i.e. in the interior and immediate vicinity of the positioning system or head clamp, and used as the tracking field of an electromagnetic tracking system. Said electromagnetic tracking system, and/or any other tracking system (for example, an optical tracking system), can be used with a medical navigation system within the framework of the present invention. Only the generated field or the tracking references of these tracking systems are relevant to the system and method of the present invention, hence only these are shown in the drawing. Other tracking system components or the components of the medical navigation system would not have any influence on the configuration of the elements shown, hence instead of for example showing them merely as black boxes, these other components have not been shown in the drawing at all.

As has been mentioned above, the field-generating elements of the field generator are located on the interior side of the shield 2; in the embodiment shown, four such field-generating elements are illustrated and indicated by the reference numeral 1. It should be noted that such field-generating elements can be elements of conventional electromagnetic field generators and can include field-generating coils or arrangements of more than one coil in any one field-generating element 1.

In the embodiment shown, all of the parts of the patient positioning system have a pre-determined and constant position with respect to each other and with respect to the field to be generated and with respect to the patient to be immobilised in the head clamp. Thus, the aforementioned advantages of easy handling, accurate pre-calibration and compensation and a high level of tracking accuracy can be implemented in a highly compact and manageable system. Integrating the electromagnetic field generator into the head clamp is for example superior to merely attaching it loosely, as proposed in the prior art, since it enables the positions of the field-generating coils in geometrical locations around the patient's head to be optimised. The field can therefore be optimally located with respect to the region of interest, which further improves the accuracy of the tracking system and reduces distortion from the exterior or from exterior devices such as surgical microscopes. Any distortion or interference caused by parts of the system itself, for example by the shield 2, can be determined in a calibration procedure during the manufacturing process and then correspondingly compensated for when using the system.

The FIGURE shows an optical reference unit 7 to the right of the positioning system 10. Said optical tracking reference 7 comprises a reference marker array 8 at one end and, at its other end, an adaptor which can be fastened to a fixation element 9 on the housing 4 of the head clamp 10.

Combining the electromagnetic tracking system and the additional optical tracking reference also of course allows optical and electromagnetic tracking to be combined and thus offers an additional layer of redundancy which further enhances the robustness and reliability of the tracking system. The optical tracking system can also be used to provide a higher degree of reliability while determining distortions and/or interference in the calibration step, since the tracking accuracy of the optical tracking system is not influenced by any of the materials or devices used during said calibration and/or compensation steps.

The invention claimed is:

1. An apparatus comprising:
   a head clamp comprising:
      a housing having a generally U-shape and defining a region of interest in the U-shape;
      a head holder bracket operatively coupled with the housing, the head holder bracket defining opposite ends and having the generally U-shape of the housing; and axially adjustable holders carried on the opposite ends of the head holder bracket, the axially adjustable holders being configured to selectively receive a head of an associated patient in the region of interest defined in the U-shape of the housing, and to hold the head of the associated patient immobilized relative to the housing;

an electromagnetic shield operatively coupled with the housing, the electromagnetic shield having the generally U-shape of the housing whereby the electromagnetic shield and the head holder bracket extend together in the generally U-shape of the housing around the region of interest; and an electromagnetic field generator carried on the electromagnetic shield, the electromagnetic field generator comprising a field generating element selectively generating an electromagnetic field in the region of interest, the field generating element having a predetermined and constant position relative to the head clamp.

2. The apparatus according to claim 1, wherein the electromagnetic shield shields the electromagnetic field generator from external electromagnetic interference and/or distortion.

3. The apparatus according to claim 2, wherein:
the plurality of field generating elements are disposed on an interior side of the electromagnetic shield directed towards the region of interest.

4. The apparatus according to claim 1, wherein the axially adjustable holders are carried directly by the opposite ends of the head holder bracket.

5. The apparatus according to claim 4, further comprising a mounting element coupled with the head holder bracket, the mounting element adapting the head clamp for selective mounting of the apparatus with an associated couch supporting the patient.

6. The apparatus according to claim 1, wherein:
the electromagnetic field generator comprises a plurality of field generating elements located on an interior side of the electromagnetic shield towards the region of interest, the plurality of field generating elements being carried and arranged on the housing corresponding to geometrical locations around the head of the associated patient selectively disposed in the region of interest;
the axially adjustable holders are carried directly by the opposite ends of the head holder bracket; and
a portion of the head holder bracket defines a mounting element coupled with the head holder bracket, the mounting element adapting the head clamp for selectively mounting to an associated couch supporting the patient.

7. The apparatus according to claim 6, wherein the head clamp, the electromagnetic shield, the head holder bracket, and the mounting element have predetermined and constant positions relative to each other.

8. The apparatus according to claim 1, wherein the head clamp and the electromagnetic field generator are integrated with each other.

9. The apparatus to claim 1, wherein the head clamp and the electromagnetic field generator are integrally mounted, one on top of the other.

10. The apparatus according to claim 1, wherein:
the head clamp and the electromagnetic field generator are integrally mounted on a carrier element, and the housing of the head holder comprises a shell of the apparatus.

11. The apparatus according to claim 1, wherein the electromagnetic shield is located on an outside of the electromagnetic field generator as viewed from a center portion of the electromagnetic field selectively generated by the electromagnetic field generator in the region of interest.

12. The apparatus according to claim 1, wherein the electromagnetic shield is mounted on the housing, either:
within the housing of the head clamp; or
on a periphery of the housing of the head clamp.

13. The apparatus according to claim 1, further comprising:
an optical tracking reference assigned to or positioned on the apparatus.

14. The apparatus according to claim 1, wherein:
the electromagnetic field generator comprises a plurality of field generating elements carried and arranged on the electromagnetic shield at locations corresponding to geometrical locations around the head of the associated patient selectively disposed in the region of interest.

15. A method for navigating a patient or a part of the patient's body by means of a medical navigation system, the method comprising:
providing an apparatus according to claim 1; and
calibrating the apparatus, the calibrating comprising:
determining a distortion and/or interference created by elements of a certain configuration of the apparatus; and
compensating the determined interference and/or distortion as compensated distortion and/or interference for use of the apparatus in said certain configuration.

16. The method according to claim 15 further comprising determining the compensated distortion and/or interference prior to using the apparatus in said certain configuration.

17. The method according to claim 15, further comprising:
assigning to or positioning an optical tracking reference on the apparatus;
determining a distortion and/or interference created by the optical tracking reference; and
tracking the patient or the part of the patient's body with the optical tracking reference.

18. The method according to claim 15, further comprising:
positioning, by the apparatus, the patient or the part of the patient's body at a selected location relative to the electromagnetic field generator.

* * * * *